(12) United States Patent
Ledden et al.

(10) Patent No.: US 10,472,403 B2
(45) Date of Patent: Nov. 12, 2019

(54) PROTEOLYTIC DIGESTION OF CARDIAC TROPONIN I

(71) Applicant: Siemens Healthcare Diagnostics Inc., Tarrytown, NY (US)

(72) Inventors: David Ledden, Medway, MA (US); Eric Cowden, Millis, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 217 days.

(21) Appl. No.: 15/535,964

(22) PCT Filed: Dec. 23, 2015

(86) PCT No.: PCT/US2015/000485
§ 371 (c)(1),
(2) Date: Jun. 14, 2017

(87) PCT Pub. No.: WO2016/105575
PCT Pub. Date: Jun. 30, 2016

(65) Prior Publication Data
US 2017/0369544 A1 Dec. 28, 2017

Related U.S. Application Data

(60) Provisional application No. 62/095,940, filed on Dec. 23, 2014.

(51) Int. Cl.
| | |
|---|---|
| *C12N 9/50* | (2006.01) |
| *A61K 38/48* | (2006.01) |
| *C07K 14/475* | (2006.01) |
| *C12Q 1/37* | (2006.01) |
| *G01N 33/68* | (2006.01) |

(52) U.S. Cl.
CPC .............. *C07K 14/475* (2013.01); *C12Q 1/37* (2013.01); *G01N 33/6887* (2013.01); *G01N 2333/4712* (2013.01); *G01N 2333/976* (2013.01)

(58) Field of Classification Search
CPC ........ A61K 38/48; A61K 38/482; C12N 9/50; C12N 9/6424; C12N 9/6427; C12Y 304/21; C12Y 304/21001
See application file for complete search history.

(56) References Cited

U.S. PATENT DOCUMENTS

| 5,660,798 A | 8/1997 | Doshi et al. |
|---|---|---|
| 2004/0106150 A1 | 6/2004 | Wang |
| 2007/0049739 A1 | 3/2007 | Troxel et al. |
| 2007/0093443 A1 | 4/2007 | Madison et al. |
| 2009/0136511 A1 | 5/2009 | Santos Savio et al. |
| 2012/0156799 A1 | 6/2012 | Komarek et al. |

FOREIGN PATENT DOCUMENTS

| DE | 102012223378 A1 | 6/2014 |
|---|---|---|
| EP | 1843156 A2 | 10/2007 |
| WO | 9723780 A1 | 7/1997 |
| WO | 0074575 A1 | 12/2000 |
| WO | 03104251 A2 | 12/2003 |

OTHER PUBLICATIONS

Horwitt. 1944; Reactions of trypsin and chymotrypsin with heparin, trypsin inhibitor, and hexylrescorcinol. Journal of Biological chemistry. 156:427-432.*
Lefkowitz et al. 2010; Whole blood assay for elastase, chymotrypsin, matrix metalloproteinase-2, and matrix mealloporeinase-9 activity. Anal. Chem. 82: 8251-8258.*
Torchilin et al. 1978; Enzyme immobilizations on Heparin. Journal of Biomedical Materiasl12: 585-590.*
Tsou. 1951; Cytochrome c modified by digestion with proteolytic enzymes. Biochemical Journal. 49(3): 362-367.*
International Search Report and Written Opinion of International Application No. PCT/US2015/000485 dated Mar. 21, 2016.
Dubitsky et al., "Use of VividTM Plasma Separation Membrane for Sensitive Detection of Troponin in Whole Blood Samples", 2010, PALL Life Sciences, p. 1.
Examination Report of European Application No. 15873836.9 dated May 28, 2018.
Matsuda et al., "Limited Proteolysis by Chymotrypsin of Midkine and Inhibition by Heparin Binding", Nov. 1, 1996, Biochemical and Biophysical Research Communications, vol. 228, No. 1, pp. 176-181.
Volpi et al., "Qualitative and Quantitative Studies of Heparin and Chondroitin Sulfates in Normal Human Plasma", Jan. 18, 1995, Biochimica et Biophysica Acta (BBA)—General Subjects, vol. 1243, No. 1, pp. 49-58.
European Search Report and Written Opinion of European Application No. 15873836.9 dated Sep. 12, 2017.
Examination Report of European Application No. 19166453.1 dated Sep. 18, 2019.

* cited by examiner

*Primary Examiner* — Karen Cochrane Carlson
(74) *Attorney, Agent, or Firm* — Dunlap Codding P.C.

(57) ABSTRACT

A fluid sample container comprising a protease, when a sample fluid is placed in the fluid sample container the protease breaking a target analyte in the sample fluid into at least two peptides, the at least two peptides being smaller than the original target analyte.

5 Claims, 2 Drawing Sheets

Specification includes a Sequence Listing.

PROTEOLYTIC DIGESTION OF CARDIAC TROPONIN I

The subject application claims benefit under 35 USC § 119(e) of U.S. Provisional Application No. 62/095,940, filed Dec. 23, 2014. The entire contents of the above-referenced patent application are hereby expressly incorporated herein by reference.

BACKGROUND

1. Field of the Disclosure

This disclosure relates to improving analytical recovery of analytes during whole blood filtration and immunoassay analysis.

2. Brief Description of the Related Art

The inventive concepts described herein relate to a variety of diagnostic assays which seek to identify and qualify a target analyte in a medical patient's fluid sample.

BRIEF DESCRIPTIONS OF THE DRAWINGS

FIG. 1 illustrates a cardiac troponin I (cTnI) molecule.

FIG. 2 illustrates an cTnI molecule that has been broken into more than one peptides.

DETAILED DESCRIPTION OF THE INVENTIVE CONCEPT(S)

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As used herein, the term "fluid sample" and variations thereof is intended to include, for example, but not limited to, biological fluids (such as urine and whole blood), chemical fluids, chemical substances, suspensions, solutions, slurries, mixtures, agglomerations, tinctures, slides, or other preparations of biological fluids, synthetic analogs to biological fluids, and combinations thereof.

Finally, as used herein any reference to "one embodiment," "an embodiment," or the like means that a particular element, feature, structure, or characteristic described in connection with the embodiment is included in at least one embodiment. The appearances of the phrase "in one embodiment" in various places in the specification are not necessarily all referring to the same embodiment.

As will be appreciated by those skilled in the art, the inventive concepts described below can be applied to a variety of diagnostic assays which seek to identify and qualify a target analyte in a fluid sample. For purposes of this disclosure a target analyte should be understood as one or more of the following molecules: proteins, peptide, peptides, amino acids, and other types of amino acid analogues. A diagnostic assay should be understood as a procedure by which the amount of a target analyte in the fluid sample is quantified. Typical diagnostic assays begin after a fluid sample has been obtained from a patient and placed in a fluid sample container. When the fluid sample is whole blood this is typically performed by coupling the fluid sample container to a syringe. One such fluid sample container for whole blood is known as a "green top" sample tube and contains heparin—which prevents the whole blood sample from clotting. Next, the fluid sample can be inserted into a medical device (such as an analyzer) which performs the remaining steps of the assay. The medical device may utilize a disposable insert (sometimes referred to as a consumable or cartridge) during the performance of assay. Alternatively, the fluid sample can be inserted into the disposable insert—which is then inserted into the medical device.

In one embodiment of the invention the fluid sample is moved through a filtration device to arrive at a filtered fluid sample. This filtration can be performed using capillary action or a pumping means disposed within the medical device. In the case of whole blood, the filter outputs plasma that is substantially free of Red Blood Cells (RBCs). Illustrative filtration devices include one or a combination of: a filter, a pre-filter, and/or an asymmetric membrane (ASM)—which contains pores of varying sizes. Filtration device(s) may be disposed in the medical device, the disposable insert, or a combination of both. Once filtered, the amount of the target analyte in the filtered fluid sample is determined through the appropriate use of antibodies, reagents, and electrochemical sensors. In another embodiment of the invention, the fluid sample can be subjected to centrifugation.

An illustrative class of diagnostic assays relate to troponin. Intact troponin in whole blood is an intracellular muscle protein with three subumits [i.e., TnI (Inhibitory Subunit), TnT (Tropomyosin Binding Subunit) and TnC (Calcium Binding Subunit)]. It should be noted that there are specific subunits for cardiac muscle (i.e., cTnI and cTnT) but not for TnC which is the same in all types of muscles.

An illustrative type of diagnostic assay relating to cardiac muscle is a cardiac troponin (cTn) assay which determines the level of cTn protein molecules (i.e., the target analyte) in a fluid sample of whole blood. The detection of a rise and/or fall of cardiac troponin plays a key role in the early diagnosis and management of myocardial infarction (MI) and acute coronary syndromes (ACS). Cardiac troponins, such as cardiac troponin I (cTnI) and cardiac troponin T (cTnT) protein molecules are proven biomarkers for the diagnosis and management of MI and ACS. Examples of cTn assays include, but are not limited to, cTnI assays, cTnT assays, and combined cTnI/cTnT assays—each of which target different cTn molecules or combinations of cTn molecules. A cTnI assay determines the level of cTnI molecules in a fluid sample of whole blood. A cTnT assay determines the level of cTnT molecules in a fluid sample of whole blood. A combined cTnI/cTnT assay determines the levels of cTnI and cTnT molecules in a fluid sample of whole blood. Certain cTn assays may also measure one ore more subunits of troponin (such as TnI)—even when that subunit is complexed to another subunit (such as TnT or TnC).

Like many other diagnostic assays, in current cTn assays a fluid sample of whole blood is first obtained from a patient. Typically this sample is obtained using a "green top" sample tube containing heparin—which prevents the whole blood from clotting. Next, the whole blood is inserted into a medical device (such as an analyzer) and/or the disposable insert. Upon receiving the fluid sample of whole blood, the whole blood is filtered in order to arrive at plasma that is substantially free from RBCs. Illustrative filtration devices remove RBCs from whole blood and include one or a combination of: a pre-filter, a filter, and/or an asymmetric membrane (ASM)—which contains pores of varying sizes. Once filtered, the amount of the target analyte (i.e., cTnI, cTnT or cTnI/cTnT molecules) in the plasma is determined through the use of specific antibodies which bind to specific antibody bind regions (epitopes) of the target analyte (i.e., the cTnI, cTnT or cTnI/cTnT molecules). The resulting binding pairs can be detected by a variety of detections means based on the type of technology used in the assay—illustrative detection technology includes: fluorescence, chemiluminescence, electrochemical luminescence, electrochemically, and luminescent oxygen channeling immunoassay ("LOCI").

While current whole blood filtration techniques are able to produce the desired RBC free plasma, the inventors observed that the analytical recovery of cTnI and/or cTnT in current assays is low and inconsistent. One approach to improve recovery associated with non-specific binding is to pre-treat the filtration device with casein, sucrose and surfactant in an effort to improve the recovery of cTnI and/or cTnT from the fluid sample of whole blood. Another approach involves adding one of the anti-cTnI and/or cTnT antibodies used in the diagnostic assay to the fluid sample of whole blood sample prior to filtration. While these approaches have, to some degree, improved the analytical recovery of cTn assays, there is room for more improvement.

While working to improve the performance of cTn assays the inventors observed that a certain amount of cTn molecules were getting lost in the assay. For example, during a cTnI assay where the fluid sample of whole blood had elevated hematocrit levels—e.g., levels where Red Blood Cells (RBCs) make up an unusually high percentage of the fluid sample of whole blood—a significant percentage of cTnI was getting lost in the assay. This same phenomenon was also observed—to a lower extent—in the fluid samples of whole blood with average or slightly above/below average hematocrit levels. Without getting bound by theory, it is believed that one or more, up to all, of the following factors contribute to the loss of cTnI: (1) the assay's filtration device itself could be filtering out cTnI; (2) cTnI could be sticking to the filtration device as it is passing through; (3) RBCs that have accumulated in the assay's filtration device could be filtering out cTnI; and (4) the combination of heparin (if present in the fluid sample of whole blood), RBCs and cTnI could be binding together—the combination of which may be getting filtered out by the assay's filtration device. One or more, up to all, of the factors could be responsible for the observed low recovery of cTnI through the filtration device of an illustrative cTnI assay for a given fluid sample of whole blood.

The inventive concepts disclosed herein improve the analytical recovery of diagnostic assays during the filtration portion of the assay by breaking the target analyte in a fluid sample into two or more peptides that are smaller, more well defined molecules than the original target analyte. Two, three or more peptides can be created from the target analyte by, for example, but not limited to, using a protease (i.e., a protein that "digests" other proteins). By selecting an appropriate protease, specific peptides can be created from the target analyte by breaking the target analyte molecule at a precise location(s). As will be explained below, the appropriate protease for a given target analyte molecule creates at least one diagnostically significant peptide that functions with the underlying diagnostic assay and does not get caught up in the filtration device. For purposes of this disclosure, a peptide should be understood as containing a sequence of one or more amino acids.

For example, in order to mitigate the four possible contributing factors noted above, a protease can be used to "break" the cTn into smaller, less "sticky," molecules. By deliberately breaking the cTn molecules in the proper places (as will be explained below) the resulting peptides are (1) more likely to make it through the filtration device and (2) allow many, if not all, of the current cTn assays following whole blood filtration to properly function. Stated another way, by breaking cTn molecule into peptides the inventive concepts disclosed herein have improved the recovery of cTn molecules in cTn assays without impacting the underlying functionality of current cTn assays. These inventive concepts, therefore are compatible with most, if not all, cTn assays which use antibody bind regions (epitopes) of cTn molecules.

The separation of the target analyte (in this case cTn molecules) into peptides can take place prior to, or contemporaneously with, filtration of the fluid sample of whole blood. For example, the protease can be mixed with the fluid sample in the fluid sample container by placing the protease in the fluid sample container before or after the fluid sample is placed therein. In one example, a fluid sample container containing both heparin and a protease may be provided to a medical professional for fluid sample collection. Alternatively, the liquid sample and the protease may be mixed by the medical device prior to filtration or within the disposable insert. The protease can also be disposed within the filtration device so that the target analyte is broken into peptides during filtration.

The disposable insert discussed above may be single or multi use. The disposable insert contains compounds and/or components for use by the medical device during a diagnostic assay. For example, the disposable insert can contain one or both of the protease and the filtration device(s). An illustrative disposable insert includes, at least, a sample fluid entry port, a protease reservoir, a chamber in which the protease and fluid sample can be combined (which may be the protease reservoir itself), a filtration device, an analysis chamber (where the output of the filtration device can be interrogated by the medical device), and fluidic pathways connecting each of the aforementioned features. An alternative illustrative disposable insert includes, at least, a sample fluid entry port, a filtration device containing the appropriate amount of protease, an analysis chamber (where the output of the filtration device can be interrogated by the medical device), and fluidic pathways connecting each of the aforementioned features.

In various other embodiments, various aspect of the inventive aspects described herein may be performed by a combination of the medical device and the disposable insert in a wide variety of ways that should be apparent to those skilled in the art. In one embodiment, separation of the target analyte into peptides and filtration of the fluid sample can take place in the medical device. In other embodiments, the separation of the target analyte into peptides and filtration of the fluid sample takes place in the disposable insert. In another embodiment, the disposable insert may contain the filtered sample for inspection by the medical device.

Figure 1:
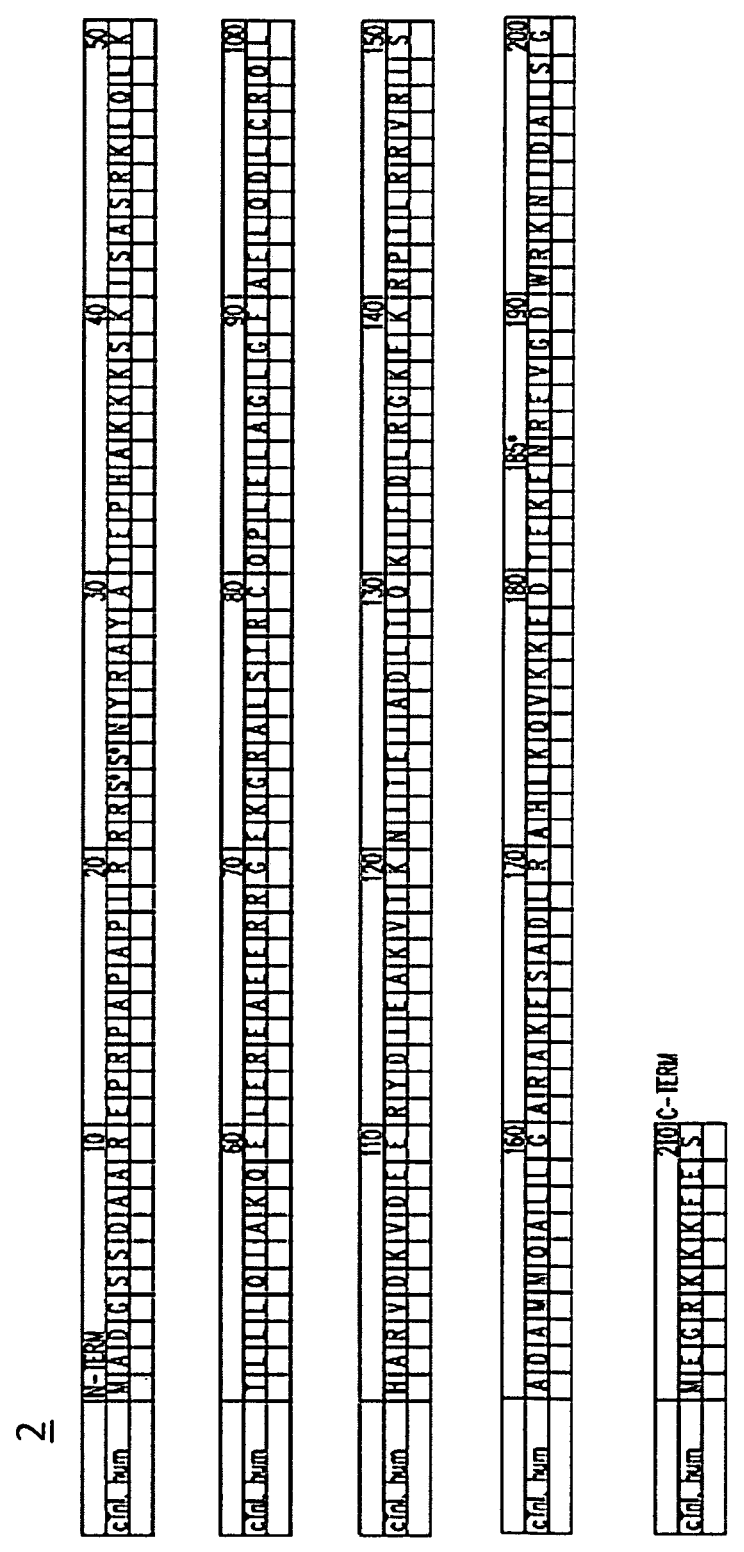

Using a cTnI molecule as an example of a cTn molecule, FIG. 1 depicts a map of the sequence of amino acids (shown by position numbers 1-210) which comprise a cTnI molecule 2. In FIG. 1, the following abbreviations are used: A—Alanine, R—Arginine, N—Asparagine, D—Aspartic acid (Aspartate), C—Cysteine, Q—Glutamine, E—Glutamic acid (Glutamate), G—Glycine, H—Histidine, I—Isoleucine, L—Leucine, K—Lysine, M—Methionine, F—Phenylalanine, P—Proline, S—Serine, T—Threonine, W—Tryptophan, Y—Tyrosine, V—Valine, B—Aspartic acid or Asparagine, Z—Glutamine or Glutamic acid, and X—Any amino acid. Additionally, 'TERM' refers to a termination codon.

Continuing with FIG. 1, according to the inventive concepts disclosed herein, two, three or more peptides can be created from the cTnI molecule 2 by introducing a protease. By selecting an appropriate protease, specific peptides 4 can be created from the cTnI molecule 2 by breaking the cTnI molecule at a precise location(s). For example, the cTnI molecule can be broken into one, two, three, four, five, or more peptides.

Figure 2:
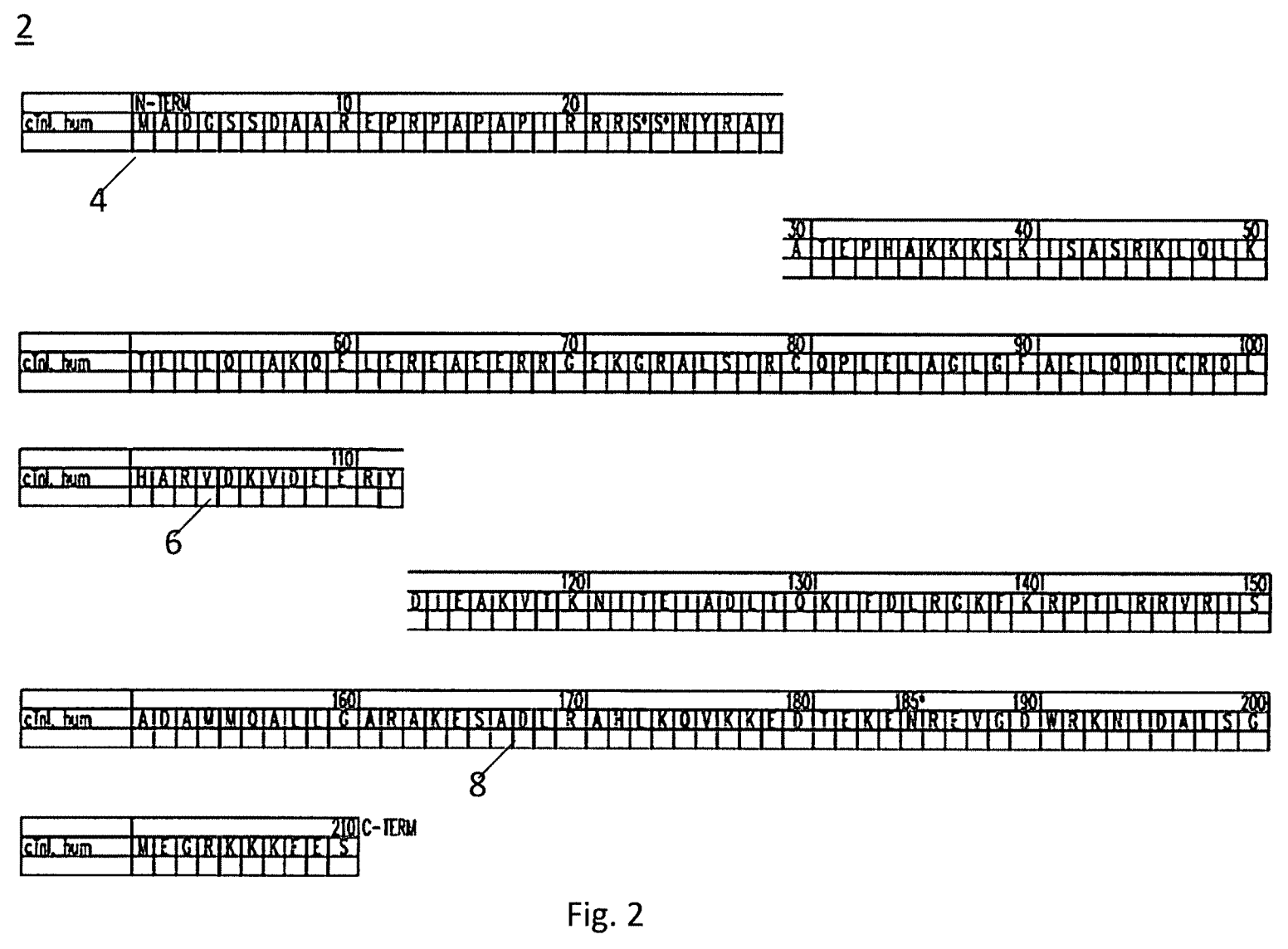

FIG. 2 illustrates a cTnI molecule 2 that has been broken into three peptides 4, 6, and 8. In this embodiment, the cTnI was digested in order to separate out the middle portion of the cTnI molecule (e.g., peptide 6) which is the string of amino acids extending from approximately position number 30 to position number 112. This middle portion 6 of the cTnI molecule is stable and contains enough of the characteristic of the original cTnI molecule to allow existing antibody binding regions (epitopes) of certain cTnI assays to yield results—thus making it a diagnostically significant portion of the cTnI molecule. Based on the sequence of cTnI shown in FIG. 1, the illustrative protease chymotrypsin cleaves proteins at aromatic hydrophobic amino acids (e.g., tyrosine—Y, tryptophan—W and phenylalanine—F) and yields proteolytic fragments (e.g., peptides 4 and 8) that leave the stable, middle portion (peptide 6) of the cTnI molecule intact. Generally speaking a protease cleaves an amino acid at one or both of the C-Terminal side or the N-Terminal side. It is believed that the protease chymotrypsin cleaves on the C-Terminal side. In FIG. 2, the beginning of cTnI molecule 2 is broken off and represented by peptide 4 (position numbers 1 through 29) and the end of cTnI molecule 2 is broken off and resented by peptide 8 (position numbers 113 through 210)—e.g., on the-Terminal of the tyrosine Y amino acid. Heparin, which may be mixed with the fluid sample at some point in the diagnostic assay, binds to RBCs and cTnI molecules between position numbers 113 and 210 (i.e. in peptide 8). By separating and allowing heparin to bind to peptide 8, rather than the entire molecule, diagnostically significant portions of the cTnI molecule (i.e., middle peptide 6) are able to pass through the filtration device while the combination of heparin, peptide 8, and RBCs gets filtered out. While peptides 4 and 8 are shown as remaining intact, it should be appreciated that peptides 4 and 8 may be further broken down into smaller peptides depending on the protease used. Heparin binds to cTnT in a similar manner—thus allowing for the diagnostically significant portion of the cTnT molecule to pass through the filtration device in a cTnT assay as well.

It should be noted that chymotrypsin protease can also cleave proteins at Leucine—L and methionine—M amino acids residues (note that in the sequences shown in FIGS. 1 and 2 each amino acid is considered a residue). This cleaving has the potential to break peptide 6 in FIG. 2 into smaller peptides—which would negatively impact current assay results. However, the the amount of cleaving at leucine—L and methionine—M amino acid locations is notably lower than the cleaving which otherwise takes place at aromatic hydrophobic amino acids. Thus a large enough number of diagnostically significant peptides 6 are formed to allow for most, if not all, of cTn assays to function properly.

According to one embodiment of the invention, the antibody is bound to the cTnI molecule prior to proteolytic digestion to protect the epitope. When the antibody is bound to one of the epitopes it will prevent the protease from digesting that portion of the amino acid sequence. This also permits one of the binding events (the creation of the antibody:analyte complex) in the assay to be completed before or during the sample filtration process. It is possible that the protease could digest a portion of the antibody involved in the antibody:analyte complex but is unlikely that complex would fall apart.

As should be appreciated by a person skill in the art, while the above text describes the inventive concepts in relation to cTn assays, the inventive concepts disclosed herein improve the recovery (as described above) are equally applicable to a wide variety of other diagnostic assays which target specific molecules that are prone to getting trapped in the assay's filtration device. Furthermore, the inventive concepts disclosed herein should also be understood as extending to diagnostic assays in which a filtration device does not contribute the loss of the target analyte. Possible reasons for this include instances where a filter is not present in the diagnostic assay or where a filter is present but does not filter, trap or otherwise prevent enough of the target analyte from passing through to have a measurable impact on the diagnostic assay itself. In any of these instances, certain diagnostic assays may still benefit from the use of a peptide to break the target analyte in a fluid sample into two or more peptides that are smaller, more well defined molecules than the original target analyte. Detecting these smaller peptides may be, for example, easier or otherwise more reliable than detecting the target analyte itself.

The following is a non-limiting list of illustrative embodiments of the inventive concepts disclosed above:

1. A fluid sample container comprising: a protease, when a sample fluid is placed in the fluid sample container the protease breaking a target analyte in the sample fluid into at least two peptides, the at least two peptides being smaller than the original target analyte.

2. The fluid sample container of illustrative embodiment 1 further comprising: heparin, when the sample fluid is whole blood the heparin preventing red blood cells in the whole blood sample from clotting upon introduction of the fluid sample into the fluid sample container, the heparin binding to less than all of the at least two peptides.

3. The fluid sample container of any of illustrative embodiments 1 to 2, wherein the protease is chymotrypsin and the target analyte is a cardiac troponin (cTn) molecule.

4. The fluid sample container of illustrative embodiment 3, wherein the cTn molecule is at least one of troponin I (cTnI) or cardiac troponin T (cTnT).

5. A device comprising: a sample fluid filter; and a protease, wherein when a sample fluid is mixed with the protease, the protease breaking a target analyte in the sample fluid into at least two peptides, the at least two peptides being smaller than the original target analyte.

6. The sample fluid filtration device of illustrative embodiment 5, wherein at least one of the at least two peptides is small enough to pass through the sample fluid filtration device.

7. The device of illustrative embodiment 6, wherein the sample fluid is a whole blood sample; wherein the sample fluid further contains heparin, the heparin preventing red blood cells (RBCs) in the whole blood sample from clotting, the heparin binding to individual RBCs and to at least one of the at least two peptides but less than all of the at least two peptides to form a bound compound; and wherein the sample fluid filter prevents the bound compound from flowing there through.

8. The device of any of illustrative embodiments 5 to 7, wherein the protease is disposed within the sample fluid filter.

9. The device of any of illustrative embodiments 5 to 7, wherein the protease is mixed with the sample fluid in a sample container external to the sample fluid filter.

10. The device of any of illustrative embodiments 5 to 7, wherein the protease is chymotrypsin and the target analyte is a cardiac troponin (cTn) molecule.

11. The device of illustrative embodiment 10, wherein the cTn molecule is at least one of troponin I (cTnI) or cardiac troponin T (cTnT).

12. A diagnostic assay comprising the steps of filtering a sample fluid mixture through a sample fluid filter, the sample fluid mixture comprising a sample fluid and a protease, the protease breaking a target analyte in the sample fluid into at least two peptides that are smaller than the original target analyte, the at least two peptides comprising at least a first peptide and a second peptide, the sample fluid filter allowing at least the first peptide to flow there through and preventing at least the second peptide from flowing there through to produce a filtered sample fluid mixture; and determining an amount of the first peptide in the filtered sample fluid mixture.

13. The diagnostic assay of illustrative embodiment 12, further comprising: prior to filtering, receiving the sample fluid mixture.

14. The diagnostic assay of illustrative embodiment 13, further comprising: prior to filtering, receiving the sample fluid; and prior to filtering but after receiving, mixing the sample fluid with the protease to create the sample fluid mixture.

15. The diagnostic assay of any of illustrative embodiment 12 to 14, wherein the sample fluid is whole blood and further contains heparin, the heparin preventing red blood cells (RBCs) in the whole blood sample from clotting, the heparin binding to individual RBCs and to at least the second peptide but not the first peptide to form a bound compound; and wherein the sample fluid filter prevents the bound compound from flowing there through.

What is claimed is:

1. A diagnostic assay for determining a level of cardiac Troponin I (cTnI) in a whole blood sample fluid, the assay comprising the steps of:
    (a) receiving the whole blood sample fluid comprising cTnI, wherein the whole blood sample fluid further contains heparin, wherein the heparin prevents red blood cells (RBCs) in the whole blood sample from clotting, wherein the heparin binds to individual RBCs, and wherein the heparin binds to cTnI;
    (b) mixing the whole blood sample fluid of (a) with chymotrypsin to create a sample fluid mixture, wherein the chymotrypsin breaks the cTnI present in the whole blood sample fluid into at least three peptides, the at least three peptides comprising at least an N-terminal peptide fragment, a C-terminal peptide fragment, and a middle peptide fragment, wherein the heparin present in the whole blood sample fluid binds to the C-terminal peptide fragment of cTnI;
    (c) filtering the sample fluid mixture through a sample fluid filter such that the sample fluid filter prevents the heparin-bound RBCs and the heparin-bound C-terminal peptide fragment of cTnI from flowing there through and outputs the N-terminal peptide fragment of cTnI and the middle peptide fragment of cTnI that are not bound by heparin to flow there through to produce a filtered sample fluid mixture; and
    (d) determining an amount of the middle peptide fragment of cTnI in the filtered sample fluid mixture.

2. The diagnostic assay of claim 1, wherein the middle peptide fragment of cTnI has the amino acid sequence represented by SEQ ID NO:3.

3. The diagnostic assay of claim 1, wherein the C-terminal peptide fragment of cTnI has the amino acid sequence represented by SEQ ID NO:4.

4. The diagnostic assay of claim 1, wherein the step of determining an amount of the middle peptide fragment of cTnI uses a detection technology selected from fluorescence, chemiluminescence, electrochemical luminescence, electrochemically, and luminescent oxygen channeling immunoassay (LOCI).

5. The diagnostic assay of claim 1, wherein the N-terminal peptide fragment of cTnI has the amino acid sequence represented by SEQ ID NO:2.

* * * * *

SEQUENCE LISTING

```
<160> NUMBER OF SEQ ID NOS: 4

<210> SEQ ID NO 1
<211> LENGTH: 210
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
```

```
                65                  70                  75                  80
Gln Pro Leu Glu Leu Ala Gly Leu Gly Phe Ala Glu Leu Gln Asp Leu
                    85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Ala Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210

<210> SEQ ID NO 2
<211> LENGTH: 29
<212> TYPE: PRT
<213> ORGANISM: Homo sapiens

<400> SEQUENCE: 2

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr
            20                  25

<210> SEQ ID NO 3
<211> LENGTH: 83
<212> TYPE: PRT
<213> ORGANISM: Homo sapiens

<400> SEQUENCE: 3

Ala Thr Glu Pro His Ala Lys Lys Lys Ser Lys Ile Ser Ala Ser Arg
1               5                   10                  15

Lys Leu Gln Leu Lys Thr Leu Leu Leu Gln Ile Ala Lys Gln Glu Leu
                20                  25                  30

Glu Arg Glu Ala Glu Arg Arg Gly Glu Lys Gly Arg Ala Leu Ser
            35                  40                  45

Thr Arg Cys Gln Pro Leu Glu Leu Ala Gly Leu Gly Phe Ala Glu Leu
    50                  55                  60

Gln Asp Leu Cys Arg Gln Leu His Ala Arg Val Asp Lys Val Asp Glu
65                  70                  75                  80

Glu Arg Tyr

<210> SEQ ID NO 4
<211> LENGTH: 98
<212> TYPE: PRT
<213> ORGANISM: Homo sapiens

<400> SEQUENCE: 4

Asp Ile Glu Ala Lys Val Thr Lys Asn Ile Thr Glu Ile Ala Asp Leu
1               5                   10                  15
```

```
Thr Gln Lys Ile Phe Asp Leu Arg Gly Lys Phe Lys Arg Pro Thr Leu
             20                  25                  30

Arg Arg Val Arg Ile Ser Ala Asp Ala Met Met Gln Ala Leu Leu Gly
         35                  40                  45

Ala Arg Ala Lys Glu Ser Ala Asp Leu Arg Ala His Leu Lys Gln Val
         50                  55                  60

Lys Lys Glu Asp Thr Glu Lys Glu Asn Arg Glu Val Gly Asp Trp Arg
65                   70                  75                  80

Lys Asn Ile Asp Ala Leu Ser Gly Met Glu Gly Arg Lys Lys Lys Phe
             85                  90                  95

Glu Ser
```